United States Patent [19]
Jordan

[11] Patent Number: 5,461,929
[45] Date of Patent: Oct. 31, 1995

[54] TENSIOMETER

[76] Inventor: Donald J. Jordan, 113 Evergreen La., Glastonbury, Conn. 06033

[21] Appl. No.: 302,105

[22] Filed: Sep. 7, 1994

[51] Int. Cl.[6] ..................................................... G01N 3/08
[52] U.S. Cl. ................................ 73/831; 73/856; 73/828; 73/862.392
[58] Field of Search ............................. 73/828, 829, 831, 73/856, 862.391, 862.392, 862.393

[56] References Cited

U.S. PATENT DOCUMENTS

| | | | |
|---|---|---|---|
| 3,049,916 | 8/1962 | Weiner | 73/828 |
| 4,562,743 | 1/1986 | Bonine | 73/828 |

FOREIGN PATENT DOCUMENTS

| | | | |
|---|---|---|---|
| 887401 | 12/1981 | U.S.S.R. | 73/828 |
| 725731 | 3/1955 | United Kingdom | 73/829 |

*Primary Examiner*—Richard Chilcot
*Assistant Examiner*—Eric S. McCall
*Attorney, Agent, or Firm*—Chilton, Alix & Van Kirk

[57] ABSTRACT

A tensiometer engages an elongated test member at three spacially displaced points, the intermediate point being defined by a fulcrum about which the member is bent by application of a known spring force to the member at one of the other points. The spring force is coupled to the test member via a movable member which moves in a substantially frictionless manner.

16 Claims, 1 Drawing Sheet

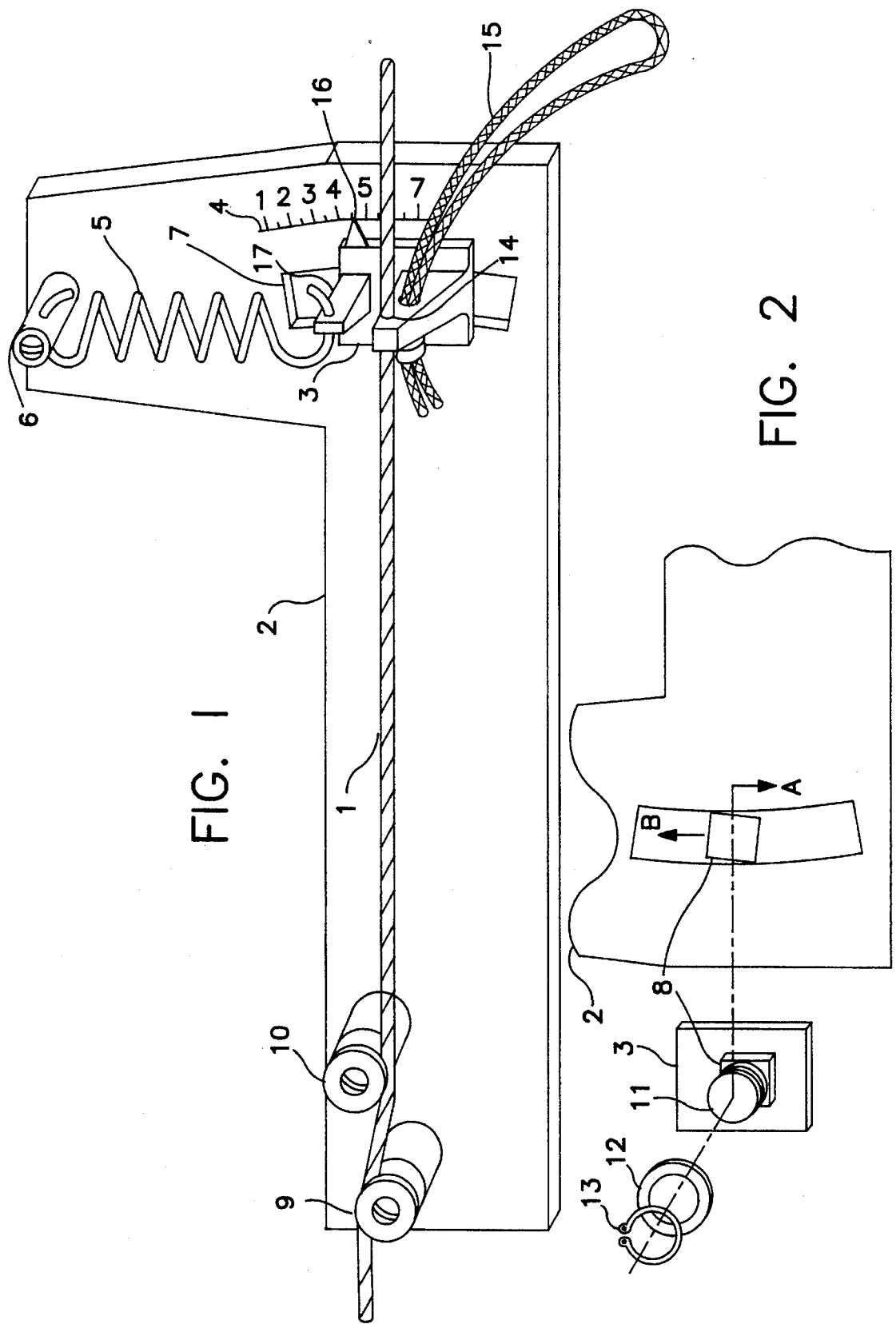

TENSIOMETER

BACKGROUND OF THE INVENTION

1. Field of the Invention

The present invention relates generally to the measurement of tension in elongated flexible members such as cables, wires, belts, straps and the like. More particularly, the present invention is directed to an easy-to-use tension measuring device and specifically to a tensiometer which, when coupled to an elongated member which is subject to a tension measurement, remains in position on that member while the tension thereof is adjusted. Accordingly, the general objects of the present invention are to provide novel and improved methods and apparatus of such character.

2. Description of the Prior Art

For a detailed description of the prior art, reference may be had to the present applicant's Pat. No. 4,135,393 issued Jan. 23, 1979. While the device of the referenced patent constituted a significant improvement over the prior art thereto, it has one notable disadvantage. Specifically, the tensiometer of U.S. Pat. No. 4,135,393 will not, absent an external influence, remain in position on an elongated member while the tension in that member is adjusted. This disadvantage has, when the tensiometer was used to measure the tension of wires or cables used to support masts on sail boats, resulted in the prior tensiometer being occasionally lost overboard.

Another prior tensiometer, particularly well suited for measuring the string tension in a sports racquet, may be seen from the present applicant's prior U.S. Pat. No. 5,133,217.

SUMMARY OF THE INVENTION

The present invention overcomes the above-briefly discussed and other deficiencies of the prior art by providing a novel and improved device for measuring the tension in elongated flexible members. A tensiometer in accordance with the present invention may easily be removably engaged with the elongated flexible member of interest and provides a pair of spaced supports for the member and a fulcrum about which the member rotates, i.e., there are three spacially displaced points of engagement of the elongated member which is under test by the instrument. In accordance with a preferred embodiment, the present tensiometer includes a unitary frame. The components which define the three points of engagement with the test member are mounted on this frame. A coil spring, supported at one end from the frame, provides a predetermined force in a direction generally transverse to the axis of the elongated flexible member under test. The second end of the spring is coupled, by means of a movable carriage, to the elongated flexible member. The carriage is mounted on the frame and defines one of the engagement points by which the tensiometer is coupled to the flexible member. The carriage will move relative to a scale provided on the frame, such movement being commensurate with the amount of deflection of the elongated flexible member caused by the known spring force. The lateral position of the carriage, accordingly, provides a visual indication of the tension in the test member.

BRIEF DESCRIPTION OF THE DRAWING

The present invention may be better understood, and its numerous objects and advantages will become apparent to those skilled in the art, by reference to the accompanying drawing wherein like reference numerals refer to like elements in the two figures and in which:

FIG. 1 is a front, perspective view of a tensiometer in accordance with the present invention; and FIG. 2 is a partial, exploded, perspective rear view of the tensiometer of FIG. 1.

DESCRIPTION OF THE DISCLOSED EMBODIMENT

With reference to the drawing, a flexible, elongated wire, the tension in which is of interest, is indicated at 1. The tensiometer of the present invention comprises a flat or planar frame member 2. The frame member 2 engages wire 1 at three points. A first of these points is defined by a fixed position support member 9. A second engagement point is defined by a second fixed position support member 10 which functions as a fulcrum. Fulcrum 10 is closely spaced to support member 9 and is located between support member 9 and the third engagement point, i.e., the point to which a known transverse force is applied to wire 1. The support member 9 and fulcrum 10 are provided with guide grooves of the appropriate size and shape to engage the elongated flexible member to be tested. Support member 9 and fulcrum 10 are attached to frame 2 in any suitable manner and can be easily replaced as necessary to accommodate wires of different diameters. In the disclosed embodiment, frame 2 is comprised of sheet metal while support member 9 and fulcrum 10 are comprised of metal or plastic.

The tensiometer engages wire 1 at a third point via a movable carriage 3, the coupling of the instrument to the wire at the third point being by means of a hook 14 integral with the carriage. Carriage 3 is mounted for movement in a slot 7 in frame 2. To this end, carriage 3 is provided with a shaft 11 which extends through slot 7. The carriage 3 is retained on frame 2 by means of a washer 12 and lock ring 13 which, as may be seen from FIG. 2, are located behind frame 2. That portion of shaft 11 which is, in the disclosed embodiment located within slot 7 is rectangular in shape as indicated at 8. In order to ensure free movement of carriage 3 along slot 7, the carriage is comprised of a suitable plastic and portion 8 of shaft 11 is sized so as to have a loose fit within the slot. In one reduction to practice of the invention, the clearance between portion 8 of shaft 11 and the side walls of slot 7 was $\frac{1}{16}$ inch.

The carriage is resiliently biased in a direction which is generally transverse to the axis of wire 1 by means of a coil spring 5. A first end of spring 5 engages a post 6 secured to an extension of frame 2. The opposite end of coil spring 5 engages an attachment means 17 on carriage 3.

The lower portion of carriage 3, i.e., the hook 14, is provided with means for manually exerting a force on the carriage, in opposition to the force of spring 5, in order to pull the carriage in the direction of the bottom of slot 7 so as to permit the wire 1 to be engaged by hook 14. In the disclosed embodiment, this means for manually moving carriage 3 comprises a nylon lanyard 15 which passes through a hole in hook 14 and is captured by knotting or the like. For the reason to be discussed below, the point of attachment of lanyard 15 to carriage 3 is offset relative to the point of application of the force of spring 5 to the carriage.

The carriage 3 is also provided with a pointer 16 which extends in a direction generally parallel to the wire 1. As carriage 3 moves along slot 7, pointer 16 will move relative to a scale 4 imprinted on or otherwise carried by frame 2. As will be described below, the position of pointer 16 relative to scale 4 indicates the tension in wire 1.

In order to measure the tension in the wire 1 or other test member, the tensiometer is positioned so that the wire 1 rests in the notches of support member 9 and fulcrum 10. The user then grasps the lanyard 15 and exerts a force to pull carriage 3 downwardly in slot 7 and extend spring 5. Upon the application of sufficient force, hook 14 on carriage 3 will move downwardly so that its position coincides with that of wire 1 whereupon the wire can be inserted into the hook. Upon release of lanyard 15, spring 5 will exert a predetermined force on member 1 thus deflecting wire 1 as shown in FIG. 1, i.e., the wire 1 will bend about fulcrum 10. The pointer 16 on carriage 3 will assume a position relative to scale 4 and this position will be an indication of the tension in wire 1.

To summarize the operation of the tensiometer of the present invention, carriage 3 defines a moveable output member which cooperates with scale 4 to provide a reading. The amount the member under test is deflected is approximately inversely proportional to the tension in the member, i.e., a wire having high tension will bend less than a similar wire having a low tension. Thus, by suitably calibrating scale 4, and knowing the force provided by spring 5, an accurate determination of the tension in an elongated flexible member 1 can be obtained.

In order to provide a precise determination of the tension in the member under test, it is necessary to avoid sliding friction between moving parts of the mechanism. In the present invention, this is accomplished by permitting carriage 3 to float freely as the wire 1 deflects. Thus, in operation of the present invention, the carriage 3 does not bear against frame 2 or the sides of slot 7 with any appreciable force. This result is achieved by holding the wire 1 parallel to the frame 2 by means of its engagement with the notches in support member 9 and fulcrum 10 and by providing clearance between the retaining washer 12 on shaft 11 and the frame 2. In order to prevent carriage 3 from bearing against the side of slot 7, liberal clearance is provided between the rectangular portion 8 of shaft 11 and the sides of the slot. Additionally, the axis of shaft 11 is positioned at the center of slot 7 when the member 1 is engaged by hook 14. This positional relationship is accomplished by offsetting the force provided by lanyard 15 from the center line of the carriage 3 as represented in FIG. 2. In FIG. 2, the force resulting from pulling downwardly on lanyard 15 is indicated at A while force B is the pull of spring 5. These offset forces result in a torque being applied to carriage 3 which will cause the rectangular portion 8 of shaft 11 to rotate in a clockwise direction within slot 7 until opposite corners of the shaft portion 8 contact the edges of the slot thereby positioning shaft 11 in the approximate center of slot 7 at the time the pull on lanyard 15 is released.

In use of the tensiometer of the present invention, when a test member 1 has been "hooked" to the carriage 3 and the lanyard 15 released, the force of spring 5 will cause carriage 3 to rotate in a counterclockwise direction to separate the corners of rectangular shaft portion 8 from the sides of slot 7. This will permit carriage 3 to move in slot 7 substantially without friction.

While a preferred embodiment has been shown and described, various modification and substitutions may be made thereto without departing from the spirit and scope of the invention. Accordingly, it is to be understood that the present invention has been described by way of illustration and not limitation.

What is claimed is:

1. A tensiometer comprising:

frame means, said frame means including an elongated guide slot, said guide slot being defined by a pair of oppositely disposed parallel walls;

a first support member affixed to and extending from said frame means, said first support member being in part sized and shaped to engage an elongated member the tension of which is to be measured;

carriage means movably mounted on said frame means, said carriage means including a projection sized and shaped to engage said elongated member, the movement of said carriage means being generally transverse to the axis of an elongated member engaged by and extending between said projection and said first support member, said carriage means further including a shaft which moves in said guide slot, said shaft having an axis which defines an axis of rotation of said carriage means, said shaft having a shape characterized by a cross-sectional dimension which exceeds the width of said slot whereby a predetermined amount of rotation of said shaft will establish contact between said shaft and said oppositely disposed walls of said guide slot;

a second support member affixed to and extending from said frame means, said second support member being in part sized and shaped to engage said elongated member, said second support member being located intermediate said first support member and said carriage means;

means applying a known force in a first direction to said carriage means;

means for selectively applying a force to said carriage means in opposition to said known force whereby said carriage means projection may be moved to a position where it may engage said elongated member, release of said selectively applied force subsequent to said engagement of said elongated member by said carriage means projection causing said elongated member to be deflected about said second support member as a function of said known force; and means providing an indication of the magnitude of the deflection of said elongated member in response to the application of said known force thereto.

2. The tensiometer of claim 1 wherein the position of said frame means relative to the elongated member will remain constant subsequent to engagement of said carriage means projection and support members with the elongated member.

3. The tensiometer of claim 1 wherein said axis of rotation of said carriage means is oriented generally transversely with respect to said elongated member and to the direction of motion of said carriage means, said means for applying a known force to said carriage means engages said carriage means at a point which will not cause rotation of said carriage means about said axis of rotation in the absence of an opposing force, and said means for selectively applying force to said carriage means engages said carriage means at a point which is offset relative to the point of application of said known force whereby said means for selectively applying force will cause said carriage means to rotate in a first direction about said axis of rotation and said means for applying a known force will cause said carriage means to rotate in a second direction which is opposite to said first direction of rotation upon removal of said selectively applied force.

4. The tensiometer of claim 1 wherein said means for applying a known force comprises a coil spring, said spring being mounted at a first end thereof from said frame means and engaging said carriage means at a second end thereof.

5. The tensiometer of claim 1 wherein said indication providing means comprises:

pointer means carried by said carriage means; and scale means carried by said frame means, said pointer means moving relative to said scale means.

6. The tensiometer of claim 1 wherein said elongated guide slot has an arcuate shape, and wherein said carriage means shaft has a rectangular cross-section.

7. The tensiometer of claim 3 wherein said means for applying a known force comprises a coil spring, said spring being mounted at a first end thereof from said frame means and engaging said carriage means at a second end thereof.

8. The tensiometer of claim 7 wherein said elongated guide slot has an arcuate shape, and wherein said carriage means shaft has a rectangular cross-section.

9. The tensiometer of claim 8 wherein said indication providing means comprises:

pointer means carried by said carriage means; and scale means carried by said frame means, said pointer means moving relative to said scale means.

10. The tensiometer of claim 9 wherein the position of said frame means relative to the elongated member will remain constant subsequent to engagement of said carriage means projection and support members with the elongated member.

11. A tensiometer comprising:

frame means, said frame means including an elongated guide slot having an arcuate shape;

a first support member affixed to and extending from said frame means, said first support member being in part sized and shaped to engage an elongated member the tension of which is to be measured;

carriage means movably mounted on said frame means, said carriage means including a projection sized and shaped to engage said elongated member, said carriage means further including a shaft which moves in said guide slot whereby said carriage means is movable in a direction generally transverse to the axis of an elongated member engaged by and extending between said projection and said first support member, said carriage means shaft having a rectangular cross-section and an axis which defines an axis of rotation of said carriage means, said axis of rotation being generally transverse to said elongated member and to the direction of motion of said carriage means along said guide slot;

a second support member affixed to and extending from said frame means, said second support member being in part sized and shaped to engage said elongated member, said second support member being located intermediate said first support member and said carriage means;

means for applying a known force in a first direction to said carriage means;

means for selectively applying a force to said carriage means in opposition to said known force whereby said carriage means projection may be moved to a position where it may engage said elongated member, release of said selectively applied force subsequent to engagement of said elongated member by said carriage means projection causing said elongated member to be deflected about said second support member as a function of said known force, said means for selectively applying force engaging said carriage means at a point which is offset relative to the point of application of said known force whereby said means for selectively applying force will cause said carriage means to rotate in a first direction about said axis of rotation and said means for applying a known force will cause said carriage means to rotate in a second direction which is opposite to said first direction of rotation upon removal of the selectively applied force; and means for providing an indication of the magnitude of the deflection of said elongated member in response to the application of said known force thereto.

12. The tensiometer of claim 11 wherein said means for applying a known force comprises a coil spring, said spring being mounted at a first end thereof from said frame means and engaging said carriage means at a second end thereof.

13. The tensiometer of claim 1 wherein said second support member comprises a fulcrum, the elongated member being bent about said fulcrum in response to said known force.

14. The tensiometer of claim 13 wherein said first and second support members contact opposite sides of the elongated member.

15. The tensiometer of claim 14 wherein said projection includes a groove for engaging the elongated member whereby the position of said frame means relative to the elongated member will remain constant subsequent to engagement of said carriage means projection and support members with the elongated member.

16. The tensiometer of claim 15 wherein said means for applying a known force comprises a coil spring, said spring being mounted at a first end thereof from said frame means and engaging said carriage means at a second end thereof.

* * * * *